(12) United States Patent
Jansen et al.

(10) Patent No.: US 7,491,197 B2
(45) Date of Patent: Feb. 17, 2009

(54) FLUID TRANSFER DEVICE

(75) Inventors: Hubert Jansen, Stolberg (DE); Uwe Wortmann, Marburg (DE)

(73) Assignee: CSL Behring GmbH, Marburg (DE)

( * ) Notice: Subject to any disclaimer, the term of this patent is extended or adjusted under 35 U.S.C. 154(b) by 319 days.

(21) Appl. No.: 10/793,210

(22) Filed: Mar. 5, 2004

(65) Prior Publication Data

US 2004/0225274 A1  Nov. 11, 2004

(30) Foreign Application Priority Data

Mar. 6, 2003  (DE) ............................... 103 10 110

(51) Int. Cl.
*A61B 19/00* (2006.01)
*A61M 5/00* (2006.01)

(52) U.S. Cl. ..................... 604/413; 604/412; 604/246

(58) Field of Classification Search ......... 604/403–416, 604/4.01–6.16, 246, 248, 27, 32, 82–92; 206/363–366; 222/188
See application file for complete search history.

(56) References Cited

U.S. PATENT DOCUMENTS

| | | | | |
|---|---|---|---|---|
| 3,757,981 A | * | 9/1973 | Harris et al. | ................. 215/247 |
| 4,423,741 A | * | 1/1984 | Levy | ........................... 600/581 |
| 4,883,483 A | | 11/1989 | Lindmayer | |
| 5,113,904 A | * | 5/1992 | Aslanian | ..................... 137/556 |
| 5,400,923 A | * | 3/1995 | Golias et al. | ................... 222/82 |
| 5,454,409 A | * | 10/1995 | McAffer et al. | ............. 141/329 |
| 5,505,694 A | * | 4/1996 | Hubbard et al. | ............. 604/512 |
| 5,743,312 A | * | 4/1998 | Pfeifer et al. | ................. 141/329 |
| 5,833,213 A | * | 11/1998 | Ryan | ......................... 251/149.1 |
| 5,971,021 A | * | 10/1999 | Graham | ................. 137/625.48 |
| 6,022,339 A | | 2/2000 | Fowles et al. | |
| 6,240,960 B1 | * | 6/2001 | Fillmore | ...................... 137/607 |
| 6,355,023 B1 | | 3/2002 | Roth et al. | |
| 6,378,714 B1 | | 4/2002 | Jansen et al. | |
| 6,379,340 B1 | * | 4/2002 | Zinger et al. | ................. 604/246 |

(Continued)

FOREIGN PATENT DOCUMENTS

DE  690 03 805 T2  5/1994

(Continued)

OTHER PUBLICATIONS

European Search Report dated Jun. 22, 2004.

*Primary Examiner*—Leslie R Deak
*Assistant Examiner*—Phil Wiest
(74) *Attorney, Agent, or Firm*—Finnegan, Henderson, Farabow, Garrett & Dunner, L.L.P.

(57) ABSTRACT

Embodiments of the invention include a fluid transfer device, for example, for medical fluids. The device includes a housing, two piercing elements mounted in the housing, and a slide arranged between the piercing elements. The slide may be displaced with respect to the piercing elements such that, in a first position, a flow connection is established between the two piercing elements, and, in a second position, a flow connection is established between one of the piercing elements and a lateral opening of the housing. In the area of the lateral opening, the housing may have a connector for insertion of a syringe cone of a syringe. When the syringe cone is inserted into the connector, the front end of the syringe cone may move the slide from the first position to the second position.

42 Claims, 5 Drawing Sheets

U.S. PATENT DOCUMENTS

Figure 1:
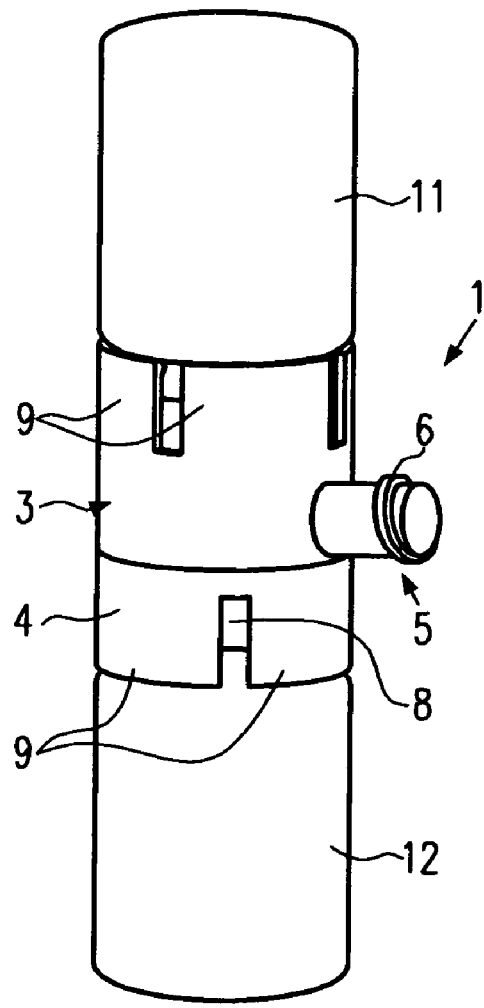

| | | | |
|---|---|---|---|
| 6,474,375 B2 * | 11/2002 | Spero et al. | 141/329 |
| 6,558,365 B2 * | 5/2003 | Zinger et al. | 604/410 |
| 6,558,385 B1 * | 5/2003 | McClurken et al. | 606/50 |
| 6,681,946 B1 * | 1/2004 | Jansen et al. | 215/249 |
| 6,875,205 B2 * | 4/2005 | Leinsing | 604/414 |
| 6,957,745 B2 * | 10/2005 | Thibault et al. | 215/249 |
| 2002/0087141 A1 | 7/2002 | Zinger et al. | |

FOREIGN PATENT DOCUMENTS

| | | |
|---|---|---|
| DE | 196 03 632 A1 | 8/1997 |
| DE | 100 57 153 A1 | 11/2000 |
| EP | 0 521 460 B1 | 1/1993 |
| EP | 0 521 461 A1 | 1/1993 |
| EP | 0 635 253 A1 | 1/1995 |
| EP | 1 145 702 A2 | 10/2001 |
| WO | 97/20536 | 6/1997 |
| WO | 99/08036 | 2/1999 |
| WO | 02/45649 A1 | 6/2002 |

* cited by examiner

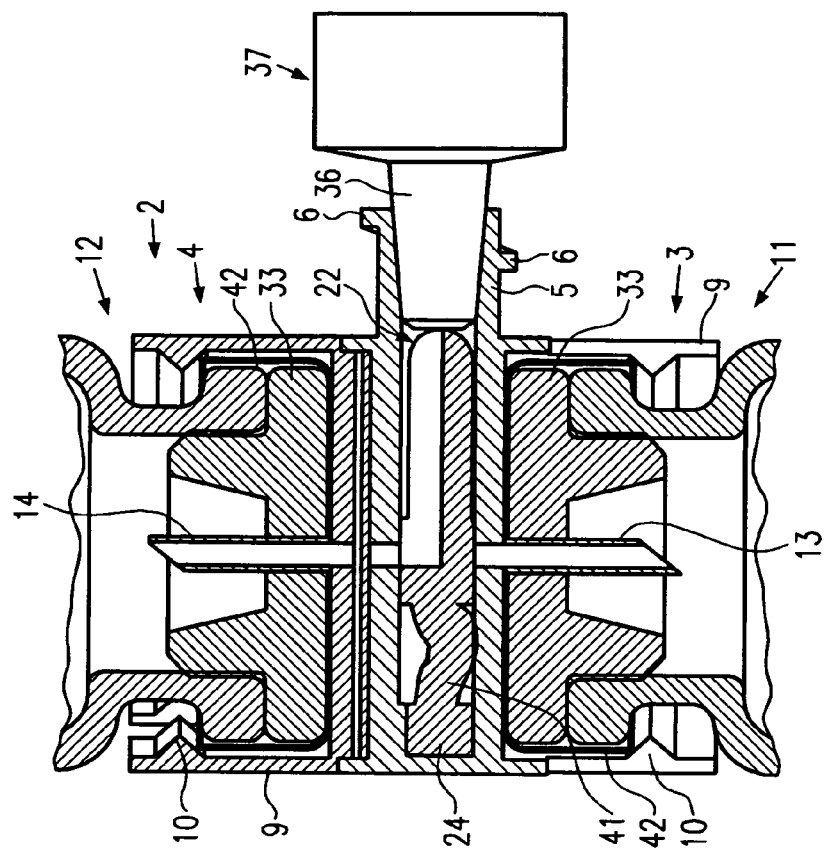
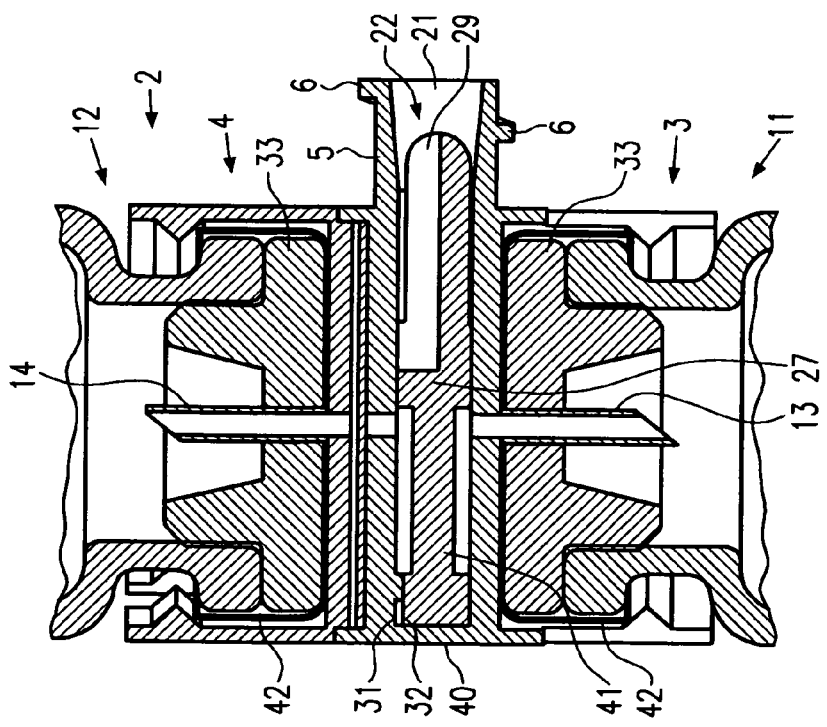
Fig.8
Fig.7

FLUID TRANSFER DEVICE

This application claims priority under 35 U.S.C. §119(a)-(d) to German Patent Application No. 10310110.1 which was filed in Germany on Mar. 6, 2003, the entirety of which is incorporated herein by reference.

The invention relates to a fluid transfer device, for example for medical fluids, with a housing, with a first needle-shaped or mandril-shaped piercing element mounted in the housing, with a second needle-shaped or mandril-shaped piercing element mounted in the housing, the two piercing elements pointing away from one another and having flow channels. The fluid transfer device also may include a slide which is arranged between the two piercing elements. The slide may be mounted in the housing and may be displaced with respect to the piercing elements such that, in a first position, a flow connection is established between the two piercing elements, and, in a second position, a flow connection is established between one of the piercing elements and a lateral opening of the housing.

In medical technology, it may be necessary to transfer fluid from a first container, for example a vial, to a second container, for example a vial, which contains a substance that is to be dissolved. To do so, a transfer device is inserted with the piercing elements, which are needle-shaped or mandril-shaped elements, into the closure stoppers respectively sealing the two containers and made of rubber or the like. The closure stoppers are pierced by the piercing elements, such that, in the first position of displacement of the slide, a flow connection is created between the two containers via the flow channels. The transfer of the fluid may be assisted by the fact that there is a vacuum in the inside of the container containing the substance to be dissolved. If further flow channels are routed through the piercing elements, these can serve to facilitate pressure compensation between the two containers, if there is no vacuum in the container. The transfer of the fluid takes place with the container containing the fluid located at the top, so that the fluid can pass into the container located underneath that is holding the substance to be dissolved. After the substance has dissolved, the slide is moved to the second position of displacement, and the connection between the two containers is thus blocked off. The transfer device is then turned so that the container with the dissolved substance is at the top. Since the piercing element inserted into the stopper of the container located at the top is now in flow connection with a lateral removal channel, the dissolved fluid can be removed from the vial by means of a syringe.

Such a transfer device is not only suitable for dissolving a medicament, but also for mixing two fluids, for transferring a gas, etc.

A transfer device of the type mentioned at the outset is known from EP 0 521 450 A1. There, the two piercing elements are provided with a fluid channel and also with an air channel. A slide cooperates with the fluid channel and serves directly to receive the syringe cone of a syringe. The slide is displaceable such that, in the first position of displacement of the slide, the fluid channel is freely accessible. A lip valve is fitted into the removal channel of the slide. This lip valve ensures that fluid does not escape to the outside, particularly when there is no syringe fitted in the slide. In the second position of displacement of the slide, a forwardly protruding shoulder of the slide closes off the access to the flow channel of that piercing element fitted into the container which originally received the fluid for dissolving the substance. On account of this position of the slide, the dissolved substance can be removed from the other container, past the lip valve, by means of the syringe. To guide the slide in the housing, it has a cylindrical attachment which cooperates with a corresponding cylindrical attachment of the housing.

A disadvantage of this transfer device is its complicated design. Thus, it is necessary to provide a specially designed valve with which to equip the slide. Accordingly, the structure of the slide is complicated, quite apart from the requirement that it have the projection with which the fluid channel can be blocked off. During handling, a particular disadvantage is that the syringe is connected to a movable part, namely the slide. There is therefore a danger of the slide being inadvertently moved into the first position of displacement upon removal of the fluid.

U.S. Pat. No. 6,379,340 B1 discloses a transfer device for medical fluids in which, instead of a slide, use is made of a part mounted rotatably in a housing. In a first position of rotation, the part forms a flow connection between two piercing elements and, in a second position of rotation, it forms a flow connection between one of the piercing elements and a lateral removal channel of the rotatable element. The rotatable element has a connector into which the attachment piece of a syringe can be inserted. The structure of this transfer device and its assembly are very complicated. Furthermore, handling is unsatisfactory since, because the rotatable part has to be turned for transferring the transfer set to the operating positions, it is generally unclear to the user which operative position the transfer device is in and in which direction the part is to be turned.

A transfer device with a piercing element is described in U.S. Pat. No. 6,378,714 B1. A vial is closed off with a rubber stopper, and a housing is placed onto the closed vial. The housing receives a slide with piercing element. When the cone of a syringe is inserted into the housing, the slide guided in the housing is displaced and the piercing element pierces through the seal of the vial. The fluid is able to flow through a channel formed in the piercing element and in the slide. This transfer device does not have different flow connections, on the one hand between two piercing elements and on the other hand between one piercing element and a lateral insertion opening of the housing.

The object of the invention is to develop a transfer device of the type mentioned at the outset, so that the device can be operated easily and safely by the user. It should additionally be straightforward and inexpensive to produce and assemble.

In a transfer device of the type mentioned at the outset, the object is achieved by the fact that the housing has, in the area of the lateral opening, a connector for insertion of a syringe cone of a syringe, and, when the syringe cone is inserted into the connector, the front end of the syringe cone moves the slide from the first position of displacement to the second position of displacement.

According to the invention, it is thus provided that, at the moment when the syringe is connected to the housing, the slide is displaced in the housing as a result of the movement of the syringe and in this way brings about the other functional state of the transfer device. In this state, the slide assumes the second position of displacement, in which it establishes the flow connection between one of the piercing elements and the lateral opening of the housing.

In the transfer device according to the invention, handling is particularly easy because the process of mounting the syringe on the housing in itself transfers the slide to the desired position. When the syringe is inserted, the front face of the syringe cone makes contact with the slide and displaces the latter. With the syringe inserted into the housing, movement of the slide to its first position of displacement is impossible. The fact that the syringe is inserted into the housing rules out the kind of disadvantageous and improper handling which arises in particular in the prior art in which the cone of the syringe is inserted into the slide or into the rotatably mounted part.

The structural complexity and assembly work are minimal in the transfer device according to the invention, because the slide can be made in one piece and is guided only axially in the housing.

The transfer device can be configured in a variety of ways. It is considered preferable for it to have only two piercing elements, each with a flow channel. The transfer device is thus used in connection with the transfer of a fluid into a container in which there is a vacuum. The piercing elements are designed as needles or mandrils. The resistance to penetration of the stoppers sealing the containers is thus very low.

In the area of the cone, the syringe can preferably be joined firmly to the connector of the housing. In this respect, the connector is designed in particular as a female Luer connector or Luer lock connector.

In the first position of displacement of the slide, no syringe has as yet been connected to the housing. At this time, a closure element preferably closes off the connector. This closure element is in particular a lid which can be screwed onto the connector of the housing. To prevent leaks, the closure element should seal the connector tightly. If the connector is provided with a thread, for example in order to be able to join the syringe to the connector there, the closure cap is likewise provided with a thread, so that it can be screwed onto the housing connector when the transfer set is in the functional state with the slide located in the first position of displacement.

It is considered particularly advantageous if the slide is guided in the housing. In this respect, in particular a precise sealing of the slide in relation to the housing is provided, particularly in those areas leading out from the housing. The slide can be optimally sealed off if it has a peg-shaped design. This configuration permits particularly simple assembly of the peg in the housing.

In a preferred configuration of the slide, the latter has, in the area of its circumference, a connection channel which extends at least over part of a circle and which, in the first position of displacement of the slide, connects the flow channels of the two piercing elements to one another. For production and assembly reasons, it is desirable for the slide to be designed as far as possible as a rotationally symmetrical part. In this respect, it is considered advantageous if the connection channel runs the entire circumference of the slide.

In the second position of displacement of the slide, the fluid can be led off in a particularly simple way if the slide has a removal channel which extends in the longitudinal direction of the slide and which, in the second position of displacement of the slide, is in flow connection with the flow channel of one of the piercing elements. In this respect, the slide, at a distance from the connection channel, is to be provided with the removal channel extending perpendicular to the latter. The removal channel is expediently formed by an outer slit of the slide and in particular has a V-shaped cross section. In this case the fluid does not flow through the slide, but instead between the slide and the housing.

According to a first principal embodiment of the transfer device, it is provided that the slide is rigid. In particular, the housing and the slide are made of plastic. The flow channels in the piercing elements continue through the housing to the slide. Upon insertion of the syringe into the housing, the displacement travel of the slide, when the syringe makes contact with the slide, corresponds to the distance of insertion of the syringe into the housing. In this embodiment, the slide can be fitted particularly easily if the housing has, on the side directed away from the connector for the syringe, an opening for insertion of the slide. Locking means acting between the slide and the housing should position these parts relative to one another at least in the first position of displacement. This ensures that the slide can be moved into the second position of displacement only under the action of the syringe. As long as there are no adjustment means actuated from outside the housing and acting on the slide, the latter cannot be pushed back from the second position of displacement into the first position of displacement. This is possible in a second principal embodiment of the transfer set.

According to this second embodiment, it is provided that the slide is elastic, at least in a partial area, in particular made of rubber, this partial area being deformed when the slide is moved from the first position of displacement into a second position of displacement against a stop on the housing side. The whole slide is preferably made elastic.

In this configuration of the slide and of the housing, a spring effect is obtained because the slide, upon transfer to the second position of displacement, is compressed by striking against the stop on the housing side. Thus, when the syringe is removed again from the housing, the slide, stretching back out in the longitudinal direction, follows the movement of the syringe and, with the syringe removed, resumes the first position of displacement.

The design of the slide as a component which is elastic at least in a partial area affords the particular advantage that the deformed area of the slide transmits sealing forces to the inside walls of the housing, by which means leakages of the transfer device are effectively avoided.

In this embodiment, the slide can be fitted particularly easily if the housing, on the side directed toward the connector, has an opening for insertion of the slide. The side of the housing directed away from the opening forms the stop for the slide. It is considered particularly advantageous if at least that area of the slide allocated to the connection channel is made elastic. There, the slide thus has a reduced thickness, in the sense of the above-described connection channel extending about the entire circumference of the slide.

To ensure simple handling of the containers, in particular vials, cooperating with the transfer device, the housing should, in the area of the piercing elements, have cylindrical seats for lockable insertion of the containers or of the neck of the respective vial.

To ensure that the fluid drawn into the syringe is as free from particles as possible, it is considered advantageous if a filter element is integrated into the flow path leading from the piercing element, connectable to the removal channel, to said removal channel.

Further features of the invention are set out in the patent claims, in the description of the figures, and in the figures themselves.

Figure 2:
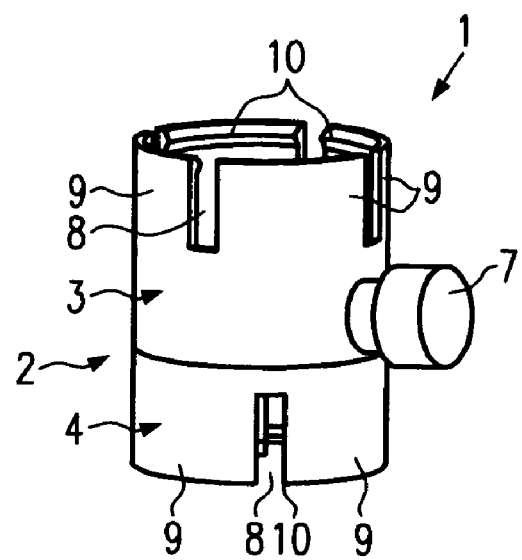
Figure 4:
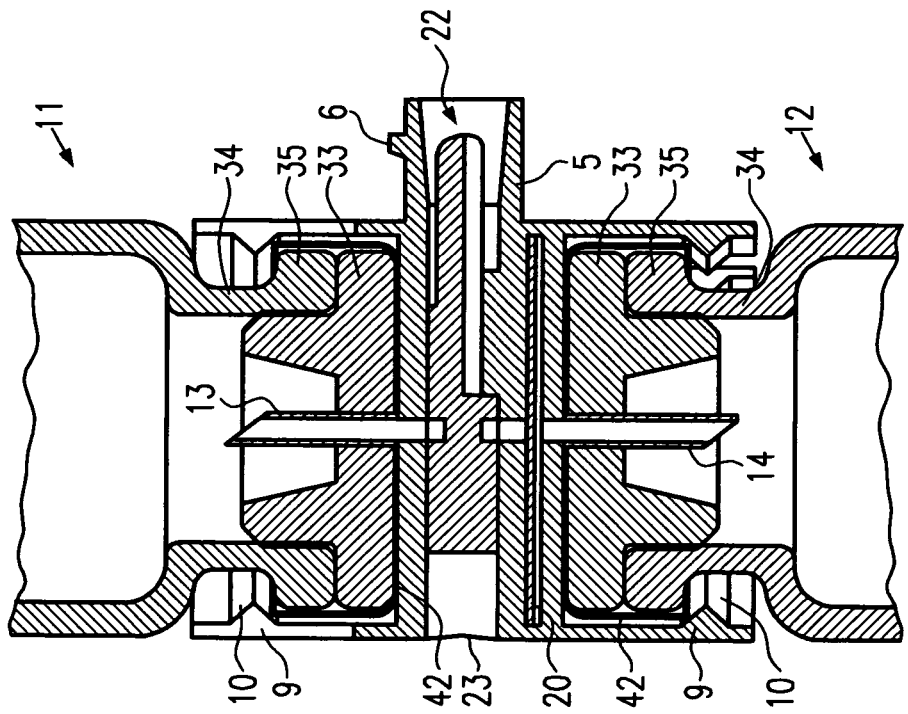
Figure 3:
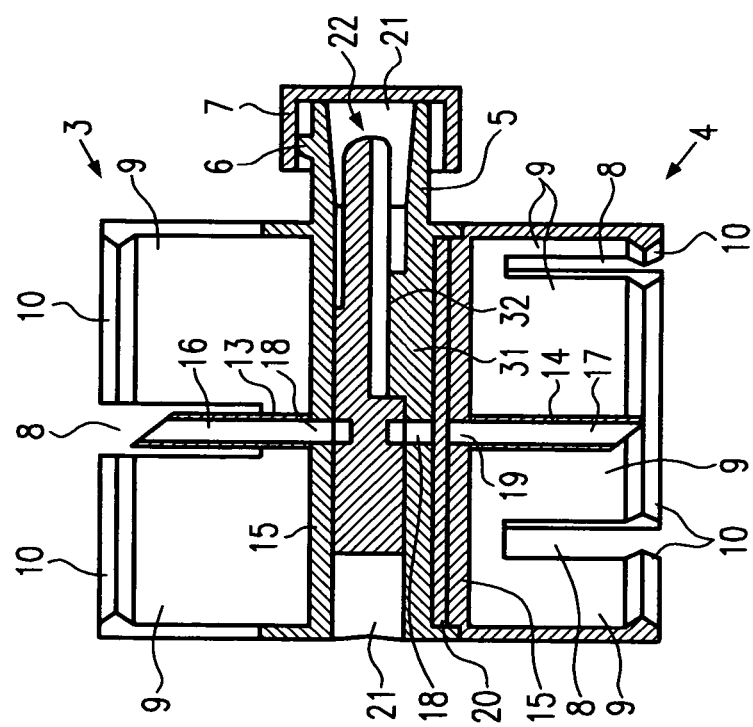
Figure 5:
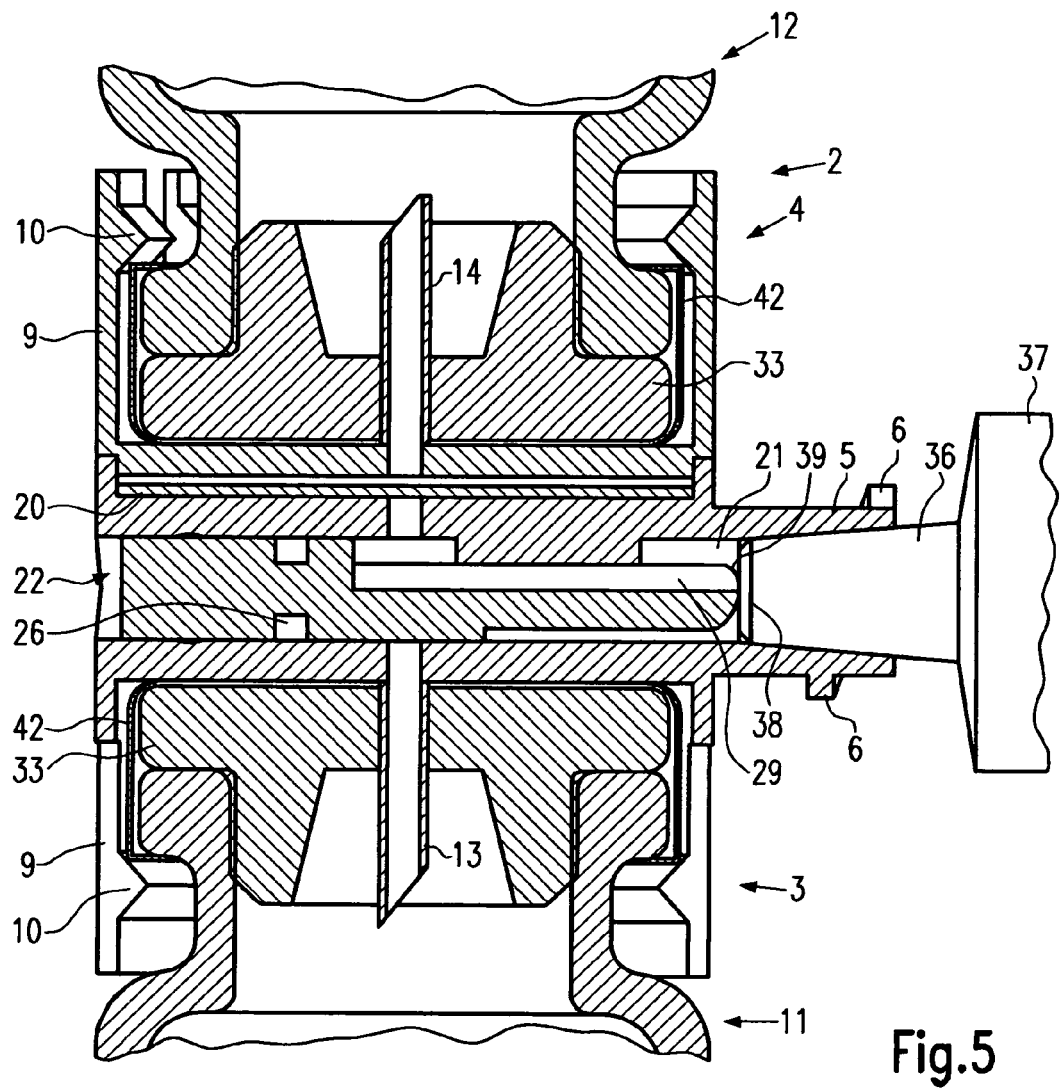
Figure 6:
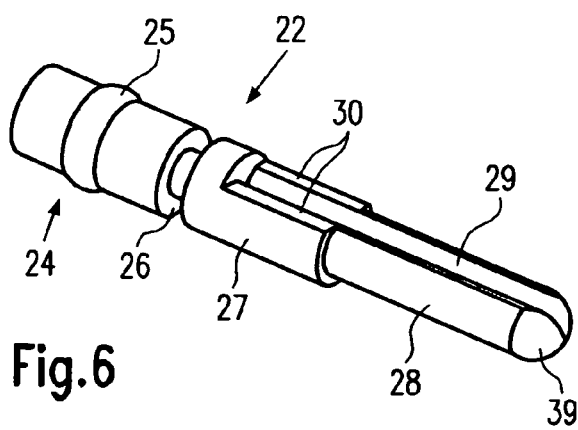
Figure 9:
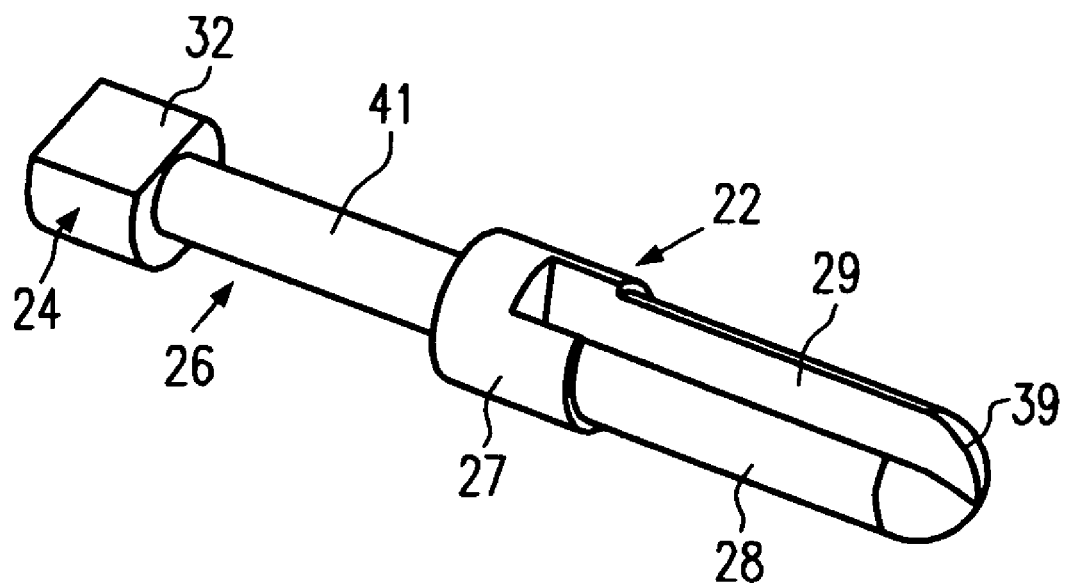

In the figures in the drawing, the invention is depicted on the basis of two illustrative embodiments, without being limited thereto. In the drawing:

FIG. 1 shows a perspective view of the transfer device, with two vials inserted in it, FIG. 2 shows a perspective view of the transfer device, FIG. 3 shows a longitudinal section through a first embodiment of the transfer device, said longitudinal section passing through the center point of the radius of the piercing elements and the longitudinal center axis of the slide, FIG. 4 shows a section through the transfer device according to FIG. 3, additionally depicting closed vials inserted into said device, in the first position of displacement of the slide, FIG. 5 shows a section according to FIG. 4, with the transfer device pivoted 180° about the longitudinal center axis of the slide, depicting the second position of displacement of the slide, and with a syringe inserted into the housing, FIG. 6 shows a perspective view of the slide used in the embodiment according to FIGS. 3 through 5, FIG. 7 shows a second embodiment of the transfer device, with vials inserted into the latter, in a cross-sectional representation according to FIG. 5, but with the slide located in the first position of displacement, FIG. 8 shows a cross-sectional representation of the second embodiment according to FIG. 7, depicting a syringe inserted into the housing, and with the slide in the second position of displacement, FIG. 9 shows a perspective view of the slide used in the second embodiment according to FIGS. 7 and 8.

In the transfer device 1 illustrated in FIGS. 1 and 2, the housing 2 is formed by two housing halves 3 and 4 which are inserted into one another and joined to one another. The housing half 3 has a lateral connector 5 with external thread 6 onto which a closure cap 7 or withdrawal syringe is screwed. In the area of the free ends, the housing halves 3 and 4 have slits 8 which extend in the longitudinal direction of the housing 2 and which between them form housing tabs 9 which, in the area of their free ends, are provided with inwardly directed locking projections 10. A glass vial 11, 12 is inserted into the respective housing half 3, 4 and secured by means of the locking projections. In the initial state, the vial 11 holds a medical fluid, for example, and the vial 12 holds a substance to be dissolved. Before the vial 12 is inserted into the transfer device 1, a vacuum in particular is created in the interior thereof.

The structure of a first embodiment of the transfer device is shown in FIG. 3. The respective housing part 3, 4 is made of plastic and forms a component part with a respective piercing mandrel 13, 14 which, in the area of the center point of the respective base plate 15 of the respective housing part 3, 4, is connected to said base plate 15. The length of the respective piercing mandrel 13, 14 is dimensioned so that it reaches as far as the locking projections 10. The flow channels 16, 17, respectively, formed in the respective piercing mandrel 13, 14 continue as portions 18, 19, respectively, in the housing parts 3, 4. Where the two housing parts 3 and 4 are inserted into one another and securely joined to one another, a flat area is formed into which a filter element 20 is fitted.

Relative to the lengthwise orientation of the housing 2, hence the lengthwise orientation of the piercing mandrils 13, 14, the housing part 3 is provided with a passage 21 extending perpendicular to these. A slide 22, shown in detail in FIG. 6, is inserted into this passage from the side directed away from the connector 5. This slide has an essentially rotationally symmetrical design. Thus, the rotationally symmetrical portion 24 of the slide 22 directed toward the rear opening of the housing part 3 has a bead 25 which, in this area, presses against the wall of the passage 21 and ensures that the slide 22 can be displaced only when a sufficient axial force is introduced into this passage. This bead 25 also seals off the slide 22 relative to the passage 21 of the housing part 3. Adjoining the front end of the rotationally symmetrical portion 24 there is a groove 26 running round the circumference of the slide 22. Adjoining this groove 26, in the direction toward the front, there is an essentially rotationally symmetrical portion 27 whose diameter corresponds to that of the rotationally symmetrical portion 24, hence that alongside the bead 25. Finally, the portion 27 is adjoined, toward the front, by an essentially rotationally symmetrical portion 28 which has a smaller diameter than the rotationally symmetrical portion 27. The portions 27 and 28 are provided with a V-shaped slit 29 which ends at a distance from the groove 26. The portion 27 is flattened in the area of the V-shaped slit 29, so that two guide surfaces 30 are formed there on both sides of the slit 29. Accordingly, as can be seen from the view in FIG. 3, the guide surface 32 of a projection 31 extending into the passage 21 cooperates with the guide surface 30 of the slide 22. consequently, the slide can only be displaced in its longitudinal direction and cannot be pivoted.

The transfer device described thus far functions in the following way:

FIG. 3 shows the transfer device 1 in the first position of displacement of the slide 22. Here, the groove 26 of the slide 22 is flush with the portions 18 in the housing part 3; the groove 26 is thus in flow connection with the flow channels 16 and 17 of the two piercing mandrils 13 and 14. The connector 5 is tightly sealed by means of the cap 7. Starting from this situation, the vial containing the fluid is first inserted into the housing part 3. An elastic stopper 33 inserted into the opening of the vial 11 is pierced by the piercing mandrel 13. In the position with the vial 11 fitted in the housing part 3, the locking projections 10 of this housing part 3 engage behind the bead 35 adjoining the neck 34 of the vial 11 on the stopper side. Before the vial 12 under vacuum and containing the medicament to be dissolved is connected to the transfer device 1, the latter is placed in the position shown in FIGS. 3 and 4, that is to say with the housing part 3 arranged at the top and with the vial 11 containing the fluid arranged at the top. The other vial 12 is then correspondingly inserted into the housing part 4, the piercing mandrel 14 piercing the stopper 33 which seals this vial 12. With the vial 12 inserted fully into the housing part 4, the locking projections 10 assigned to this housing part engage behind the bead 35 adjoining the neck 34 of this vial. Since the piercing mandrils 13 and 14 protrude into the interiors of the vials 11 and 12, the fluid is transferred, by means of the underpressure in the vial 12, from the vial 11 and through flow channel 16, groove 26 and flow channel 17 into the vial 12, and the substance located in the latter is dissolved.

As is illustrated in FIG. 4, for lateral removal of the dissolved substance from the transfer device 1, the closure cap 7 sealing the slide area on the side remote from the bead 25 is first unscrewed from the connector 5, as a result of which the vacuum is let down. The transfer device 1, with the two vials 11 and 12 fitted in it, is then turned 180° about the longitudinal axis of the slide 22 to the position shown in FIG. 5. As a result, the vial 12 with the dissolved substance in it is located at the top, and the empty vial 11 is located underneath. To remove the dissolved substance, a syringe cone 36 of a syringe 37 (only part of which is shown) is inserted sealingly into the conical opening of the connector 5, as is illustrated in FIG. 5. Upon insertion of the syringe cone 36 into the connector 5, the front end 38 of the syringe cone 36 displaces the slide 22, the syringe cone 36 making contact with a tapering end 39 of the slide 22. In the position with the syringe cone 36 inserted fully into the connector 5, the slide 22 assumes the second position of displacement, shown in FIG. 5, in which that end of the slide 22 remote from the syringe 37 is still located entirely within the housing part 3, and the flow channel 17 of the piercing mandrel 14 is now in flow connection via portions 18 and 19 with the V-shaped slit 29 in the slide 22, specifically in the area of the V-shaped slit introduced into the portion 27. Thus, when the syringe 37 is being charged, the vial 12 can be emptied via the flow connection from the piercing mandrel 14 and the V-shaped slit 29 of the slide 22.

In the embodiment according to FIGS. 3 through 6, the slide is rigid and is made in particular of plastic.

A further embodiment of the transfer device 1 is shown in FIGS. 7 through 9. This embodiment differs from the first embodiment only in terms of the slide 22 and the configuration of the housing part 3. Because of the degree of correspondence, reference is therefore made to the above description.

In the embodiment according to FIGS. 7 through 9, the slide 22 is made entirely of elastic material, in particular of a thermoplastic elastomer (TPE) or rubber. The slide 22 is inserted via the connector 5 into the housing part 3, and the latter is closed in the area of its end remote from the connector 5. This embodiment therefore does not have the opening 23 of the first embodiment. In the embodiment according to FIGS. 7 through 9, the portion 27, the portion 28 and the V-shaped slit 29 of the slide 22 are of corresponding design. The circumferential groove 26 is considerably wider than the groove 26 of the first embodiment, approximately as long as the portion 28. Correspondingly, the portion 24 is designed without a bead 25 and is much shorter than the portion 24 of the first embodiment. The portion 24 additionally has a flattened area 32 on its top, which flattened area 32 cooperates with a guide surface 31 of the housing part 3 arranged in this area. The detailed structure of the slide 22 in this embodiment is illustrated in FIG. 9.

FIG. 7 shows this embodiment in the first position of displacement of the slide, specifically in the state in which the vial 12 containing the dissolved substance has already been pivoted to the top. The slide 22 bears on the housing wall 40 remote from the connector 5. The flow connection of the flow channels 16 and 17 of the piercing mandrils 13 and 14 is obtained via the groove 26. As is illustrated in FIG. 8 and has already been explained in detail, in order to remove the dissolved substance the syringe cone 36 is inserted into the connector 5, in which process its front end makes contact with the slide 22, and, in the area of reduced cross section 41 where the groove 26 is defined, deforms the slide 22 as a result of the elastic property of said slide 22. The deformation in this area of the slide 22 and, consequently, the fact that the area of the slide 22 facing the syringe cone 36 is displaced in the direction of the housing wall 40 mean that, as is illustrated in FIG. 8, the flow channel 17 of the piercing mandril 14 comes into flow connection with the V-shaped slit 29.

In this context, an important part is played by the slide 22 preferably made of TPE. Its elastic property simplifies the sealing of the slide 22 relative to the housing part 3, so that, in both positions of displacement of the slide 22, distinct streams of fluid can be routed through the transfer device without leakages. The slide 22 made of thermoplastic elastomer has a spring effect, so that the system automatically closes when the syringe 37 is withdrawn from the connector 5. In this case, the slide 22 is immediately moved to its first position of displacement.

In the first embodiment according to FIGS. 3 through 6, in which the slide 22 is rigid, the bead 25 not only defines the respective starting position of the slide, it in particular seals off the passage 21 at the end remote from the connector 5. This is important for the function of the device. If this seal were not to function, the vacuum in the vial 12 containing the substance to be dissolved would be reduced and a transfer possible. In the embodiment according to FIGS. 7 through 9, with the elastic slide 22 and with the differently designed housing part 3, the elastic slide 22 provides direct sealing because of its material properties. In addition, the elastic slide 22 can be introduced from the removal side. In this way, the passage 21 in the area of the end of the housing 2 remote from the connector 5 can be omitted, as a result of which the sealing problem is reduced.

In both embodiments, the closure of the flow channel 16 ensures that air cannot be drawn in from the vial 11. This is important for the removal of the dissolved substance or dissolved medicament. During removal, an underpressure is generated with the syringe 37, as a result of which the dissolved substance flows into the syringe. If the vial 11 were open, the underpressure generated in the syringe 37 would be reduced and filling of the syringe 37 would thus be made considerably difficult.

Reference number 42 indicates a cap-like film seal which surrounds the bead 35 of the respective vial 11, 12 and also the stopper 33 inserted in the latter, by which means the stopper is held securely in the vial.

LIST OF REFERENCE NUMBERS 1 transfer device
2 housing
3 housing part
4 housing part
5 connector
6 thread
7 closure cap
8 slit
9 housing tab
10 locking projection
11 glass vial
12 glass vial
13 piercing mandril
14 piercing mandril
15 base plate
16 flow channel
17 flow channel
18 portion
19 portion
20 filter element
21 passage
22 slide
23 opening
24 portion
25 bead
26 groove
27 portion
28 portion
29 slit
30 guide surface
31 projection
32 guide surface
33 stopper
34 neck of vial
35 bead
36 syringe cone
37 syringe
38 end
39 end
40 housing wall
41 cross section
42 film seal

The invention claimed is:

1. A fluid transfer device, comprising:
a housing including a connector defining a lateral opening, the connector being configured to receive a syringe cone of a syringe;
first and second piercing elements mounted in the housing, each piercing element including a flow channel, the first and second piercing elements substantially pointing away from one another; and a slide disposed in the housing, at least a portion of the slide being positioned between the first and second piercing elements, wherein the slide is configured to move relative to the first and second piercing elements between a first position where the flow channel of one of the first and second piercing elements is in flow communication with the flow channel of the other of the first and second piercing elements, and a second position where the flow channel of one of the first and second piercing elements is in flow communication with the lateral opening, wherein the slide is configured such that the insertion of the syringe cone into the lateral opening of the connector moves the slide between the first position and the second position, wherein the slide is disposed in the housing in a manner that substantially prevents twisting of the slide relative to the housing, and wherein a portion of the slide defines a removal channel that is disposed on an outer portion of the slide and extends along a longitudinal axis of the slide all the way to an extremity of the slide configured to be contacted by an end of the syringe cone.

2. The fluid transfer device of claim 1, wherein at least one of the first and second piercing elements is substantially needle-shaped.

3. The fluid transfer device of claim 1, wherein at least one of the first and second piercing elements is substantially mandril-shaped.

4. The fluid transfer device of claim 1, wherein the connector is a female luer connector.

5. The fluid transfer device of claim 1, wherein the connector is configured to be closed by a closure element.

6. The fluid transfer device of claim 5, wherein the closure element is configured to close the connector in a substantially leaktight manner.

7. The fluid transfer device of claim 5, wherein the closure element is a closure cap configured to be screwed onto the connector.

8. The fluid transfer device of claim 1, wherein the housing is configured to guide the slide in a direction substantially perpendicular to a longitudinal axis of the first and second piercing elements.

9. The fluid transfer device of claim 8, wherein the housing is configured to guide the slide in a substantially sealed manner.

10. The fluid transfer device of claim 1, wherein the slide is substantially peg-shaped.

11. The fluid transfer device of claim 1, wherein the removal channel, in the second position of the slide, is in connection with the flow channel of one of the first and second piercing elements.

12. The fluid transfer device of claim 11, wherein the removal channel has a substantially V-shaped cross section.

13. The fluid transfer device of claim 1, wherein the removal channel is an angular slit.

14. The fluid transfer device of claim 1, wherein the slide is rigid.

15. The fluid transfer device of claim 1, wherein the slide is clamped in the housing.

16. The fluid transfer device of claim 1, wherein the slide is locked in the housing.

17. The fluid transfer device of claim 16, wherein the slide is locked in the housing when the slide is in the first position.

18. The fluid transfer device of claim 1, wherein the housing includes an insertion opening configured to facilitate the insertion of the slide.

19. The fluid transfer device of claim 18, wherein the insertion opening is on a side of the housing substantially opposite the connector.

20. The fluid transfer device of claim 18, wherein the insertion opening is on a substantially same side of the housing as the connector.

21. The fluid transfer device of claim 1, wherein at least a portion of the slide is elastic.

22. The fluid transfer device of claim 21, wherein the slide is made of a thermoplastic elastomer or rubber.

23. The fluid transfer device of claim 21, wherein the elastic portion of the slide is configured to be deformed when the slide is moved from the first position to the second position.

24. The fluid transfer device of claim 21, wherein the housing includes a stop configured to assist in deforming the elastic portion of the slide.

25. The fluid transfer device of claim 24, wherein the housing includes an opening configured to facilitate the insertion of the slide, wherein the opening is on a substantially same side of the housing as the connector, and wherein the stop is on a side of the housing substantially opposite the opening.

26. The fluid transfer device of claim 21, wherein substantially the entire slide is elastic.

27. The fluid transfer device of claim 21, wherein the elastic portion of the slide is configured to return the slide to the first position after the syringe cone has been removed.

28. The fluid transfer device of claim 1, wherein the slide is configured such that removal of the syringe cone from the connector moves the slide from second position to the first position.

29. The fluid transfer device of claim 1, further comprising a bead disposed around a portion of the slide.

30. The fluid transfer device of claim 29, wherein the bead seals at least a portion of an interface between the slide and the housing.

31. The fluid transfer device of claim 30, wherein the bead is disposed in a side of the housing substantially opposite the connector.

32. The fluid transfer device of claim 1, wherein the slide has a portion configured to close the flow channel of one of the first and second piercing element when the slide is in the second position.

33. The fluid transfer device of claim 1, wherein the housing includes first and second cylindrically disposed seats each configured to receive and lock at least a portion of a container.

34. The fluid transfer device of claim 33, wherein each of the first and second cylindrically disposed seats is disposed substantially adjacent one of the first and second piercing elements.

35. The fluid transfer device of claim 33, wherein each of the first and second cylindrically disposed seats is configured to receive and lock a neck of a vial.

36. The fluid transfer device of claim 1, further comprising a filter disposed in a flow path between the flow channel of one of the first and second piercing elements and the lateral opening.

37. The fluid transfer device of claim 1, wherein the slide moves in a direction substantially perpendicular to a longitudinal axis of the first and second piercing elements.

38. The fluid transfer device of claim 1, wherein the slide is disposed in the housing in a manner that substantially prevents rotation of the slide relative to the housing.

39. A fluid transfer device, comprising:

a housing including a connector defining a lateral opening, the connector being configured to receive a syringe cone of a syringe;

first and second piercing elements mounted in the housing, each piercing element including a flow channel, the first and second piercing elements substantially pointing away from one another; and a slide disposed in the housing, at least a portion of the slide being positioned between the first and second piercing elements, wherein the slide is configured to move relative to the first and second piercing elements between a first position where the flow channel of one of the first and second piercing elements is in flow communication with the flow channel of the other of the first and second piercing elements, and a second position where the flow channel of one of the first and second piercing elements is in flow communication with the lateral opening, wherein the slide is configured such that the insertion of the syringe cone into the lateral opening of the connector moves the slide between the first position and the second position, wherein the slide is disposed in the housing in a manner that substantially prevents twisting of the slide relative to the housing, wherein a portion of the slide defines a connection channel that, in the first position of the slide, is configured to connect the flow channels of the first and second piercing elements.

40. The fluid transfer device of claim 39, wherein the connection channel passes around at least a portion of the a circumference of the slide.

41. The fluid transfer device of claim 39, wherein the portion of the slide that defines the connection channel is elastic.

42. A fluid transfer device, comprising:

a housing including a connector defining a lateral opening, the connector being configured to receive a syringe cone of a syringe;

first and second piercing elements mounted in the housing, each piercing element including a flow channel, the first and second piercing elements substantially pointing away from one another; and a slide disposed in the housing, at least a portion of the slide being positioned between the first and second piercing elements, wherein the slide is configured to move relative to the first and second piercing elements between a first position where the flow channel of one of the first and second piercing elements is in flow communication with the flow channel of the other of the first and second piercing elements, and a second position where the flow channel of one of the first and second piercing elements is in flow communication with the lateral opening, wherein the slide is configured such that the insertion of the syringe cone into the lateral opening of the connector moves the slide between the first position and the second position, wherein the slide is disposed in the housing in a manner that substantially prevents twisting of the slide relative to the housing, and wherein a portion of the slide defines a removal channel that is an angular slit disposed on an outer portion of the slide.

* * * * *